(12) United States Patent
Kato et al.

(10) Patent No.: US 12,013,394 B2
(45) Date of Patent: Jun. 18, 2024

(54) IMMUNOCHROMATOGRAPHIC TEST PIECE FOR EXTRACTING AND MEASURING SUGAR CHAIN ANTIGEN, WHICH IS CAPABLE OF PREVENTING NON-SPECIFIC REACTION

(71) Applicant: Denka Company Limited, Tokyo (JP)

(72) Inventors: Daisuke Kato, Niigata (JP); Shino Muramatsu, Niigata (JP); Tomohiro Hattori, Niigata (JP)

(73) Assignee: Denka Company Limited, Tokyo (JP)

( * ) Notice: Subject to any disclaimer, the term of this patent is extended or adjusted under 35 U.S.C. 154(b) by 704 days.

(21) Appl. No.: 16/492,442

(22) PCT Filed: Mar. 14, 2018

(86) PCT No.: PCT/JP2018/009898
§ 371 (c)(1),
(2) Date: Sep. 9, 2019

(87) PCT Pub. No.: WO2018/168906
PCT Pub. Date: Sep. 20, 2018

(65) Prior Publication Data
US 2020/0049703 A1  Feb. 13, 2020

(30) Foreign Application Priority Data

Mar. 14, 2017 (JP) .................... 2017-049155

(51) Int. Cl.
*G01N 33/543* (2006.01)
(52) U.S. Cl.
CPC .............. *G01N 33/54386* (2013.01)
(58) Field of Classification Search
None
See application file for complete search history.

(56) References Cited

U.S. PATENT DOCUMENTS

| | | | |
|---|---|---|---|
| 2003/0143639 A1 | 7/2003 | Matsushita et al. | |
| 2008/0194013 A1* | 8/2008 | Shida ............... | G01N 33/54386 435/287.2 |

(Continued)

FOREIGN PATENT DOCUMENTS

| | | |
|---|---|---|
| CN | 101002095 A | 7/2007 |
| CN | 101002097 A | 7/2007 |

(Continued)

OTHER PUBLICATIONS

Merck Millipore (Rapid Lateral Flow Test Strips Considerations for Product Development; 2013) (Year: 2013).*

(Continued)

*Primary Examiner* — Rebecca M Giere
(74) *Attorney, Agent, or Firm* — Foley & Lardner LLP

(57) ABSTRACT

The present disclosure provides an immunochromatographic test piece which prevents a non-specific reaction by efficiently and continuously contacting and neutralizing a developing solution containing nitrous acid with a neutralizing reagent in an immunochromatography method of extracting and measuring a sugar chain antigen by nitrous acid extraction on the immunochromatographic test piece. The present disclosure also provides an immunochromatographic test piece for extracting and measuring a sugar chain antigen in a specimen, which comprises: a sample pad; a label region; a detection region on which the antibody against the sugar chain antigen is immobilized; a region impregnated with a neutralizing reagent upstream of the label region, and a region impregnated with a solid acid reagent or a region impregnated with nitrite, upstream of the region impregnated with the neutralizing reagent.

8 Claims, 2 Drawing Sheets

(56) References Cited

U.S. PATENT DOCUMENTS

| | | | |
|---|---|---|---|
| 2008/0206849 A1 | 8/2008 | Zak et al. | |
| 2012/0034140 A1 | 2/2012 | Ohmiya et al. | |
| 2014/0271400 A1 | 9/2014 | Cheng et al. | |
| 2014/0294930 A1* | 10/2014 | Nizet | C08B 37/0006 424/193.1 |
| 2015/0010918 A1 | 1/2015 | Ruvinsky | |
| 2015/0168397 A1 | 6/2015 | Stankov | |
| 2020/0038854 A1 | 2/2020 | Kato et al. | |
| 2020/0049703 A1 | 2/2020 | Kato et al. | |

FOREIGN PATENT DOCUMENTS

| | | |
|---|---|---|
| EP | 3 032 260 A1 | 6/2016 |
| EP | 3 324 185 A1 | 5/2018 |
| EP | 3 470 841 A1 | 4/2019 |
| EP | 3 598 130 A1 | 1/2020 |
| JP | 2001-337091 A | 12/2001 |
| JP | 2005-061910 A | 3/2005 |
| JP | 2005-331463 A | 12/2005 |
| JP | 2005-331471 A | 12/2005 |
| JP | 2014-232064 A | 12/2014 |
| JP | 2016-125875 A | 7/2016 |
| JP | 2016-161329 A | 9/2016 |
| JP | 2018-151329 A | 9/2018 |
| JP | 2018-151330 A | 9/2018 |
| JP | 2018-151331 A1 | 9/2018 |
| WO | WO 2005/121794 A1 | 12/2005 |
| WO | WO-2017/213228 A1 | 12/2017 |

OTHER PUBLICATIONS

Supplementary European Search Report dated Nov. 9, 2020 in EP 18767951.9.
Office Action and Search Report dated Apr. 8, 2022 in CN 201880018271.6.
Fujikura et al., JP2014232064A—Google translation (Year: 2014).
International Search Report dated Mar. 31, 2020 in PCT/JP2020/003065.
Office Action and Search Report dated Apr. 22, 2022 in CN 201880018199.7.
Office Action dated Feb. 26, 2021 in Indian Patent Application No. 201947040682.
Supplementary European Search Report dated Nov. 9, 2020 in EP 18767950.1.
Yamada et al., JP2005-061910A Google translation (Year: 2005).

\* cited by examiner

IMMUNOCHROMATOGRAPHIC TEST PIECE FOR EXTRACTING AND MEASURING SUGAR CHAIN ANTIGEN, WHICH IS CAPABLE OF PREVENTING NON-SPECIFIC REACTION

CROSS-REFERENCE TO RELATED APPLICATIONS

This application is the U.S. National Stage of PCT/JP2018/009898, filed Mar. 14, 2018, which claims priority to JP 2017-049155, filed Mar. 14, 2017.

TECHNICAL FIELD

The present invention relates to an immunochromatographic device for extracting and measuring a sugar chain antigen, which is capable of extracting the sugar chain antigen with nitrous acid on an immunochromatographic test piece.

BACKGROUND ART

A majority of rapid diagnostic assay involving an immunochromatography method as a principle have been broadly used as a means for promptly and simply measuring viral or bacterial infection and determining a treatment plan therefor.

In the case of such rapid diagnostic agents involving a common immunochromatography method as a principle, a specimen is suspended in a specimen suspension, and the suspension is then supplied to an immunochromatographic test piece, so that the measurement can be carried out rapidly and simply.

For detecting microorganisms belonging to genus *Streptococcus*, such as group A β-hemolytic *Streptococcus* and intraoral *Streptococcus*, it is necessary to extract a sugar chain antigen and measure the sugar chain antigen.

For example, a method, in which sodium nitrite and a neutralizing reagent are previously added to an immunochromatographic test piece, so that a nitrous acid extraction can be carried out on the immunochromatographic test piece only by the operation to suspend a specimen in an acid solution such as acetic acid and to supply the suspension to the immunochromatographic test piece, has been reported (Patent Literature 1).

Also, there is a method, in which an acid reagent and a neutralizing reagent are previously added to an immunochromatographic test piece, and a specimen is suspended in nitrite and supplied to the immunochromatographic test piece.

Most of currently commercially available group A β-hemolytic *Streptococcus* antigen detecting reagents utilizing an immunochromatography method are used in a test by mixing two solutions, namely, a nitrite solution and an acid solution, immediately before the test, to generate acidic nitrous acid, and extracting an antigen with the generated nitrous acid, or utilize a method of extracting an antigen by incorporating a pad impregnated with an acid reagent into an immunochromatographic device (immunochromatographic test piece) and generating nitrous acid on the immunochromatographic test piece. For this method, it is necessary to neutralize the generated acidic nitrous acid, and a neutralizing reagent is added in a dry state onto the immunochromatographic test piece, so that the nitrous acid is neutralized with the neutralizing reagent.

CITATION LIST

Patent Literature

Patent Literature 1: International Publication WO2005/121794

SUMMARY OF INVENTION

Technical Problem

Most of currently commercially available group A β-hemolytic *Streptococcus* antigen detecting reagents utilizing an immunochromatography method employ, in the extraction of an antigen, acidic nitrous acid generated by mixing a nitrite solution and an acid solution, and a developing solution containing the nitrous acid used in the extraction of the antigen is neutralized with a neutralizing reagent added in a dry state onto an immunochromatographic test piece, followed by an antigen-antibody reaction for measurement. However, this conventional method is problematic in that a non-specific reaction occurs.

It is an object of the present invention to provide an immunochromatographic test piece which prevents a non-specific reaction by efficiently and continuously contacting and neutralizing a developing solution containing nitrous acid with a neutralizing reagent in an immunochromatography method of extracting and measuring a sugar chain antigen by nitrous acid extraction on the immunochromatographic test piece.

Solution to Problem

The present inventor has conducted intensive studies to solve the problem of a conventional method that a non-specific reaction occurs after a lapse of a given period of time in an immunochromatography method of extracting and measuring a sugar chain antigen by nitrous acid extraction on an immunochromatographic test piece.

The present inventors have found that in the conventional method, a neutralizing reagent is completely consumed by an acid remaining upstream of an immunochromatographic test piece after a lapse of a given period of time, so that the entire developing solution on the immunochromatographic test piece is acidified, consequently causing a non-specific reaction.

Thus, the present inventors have considered that an acid used in nitrous acid extraction is neutralized reliably and continuously with a neutralizing reagent on an immunochromatographic test piece, or an acid remaining upstream of an immunochromatographic test piece is kept in the upstream portion and prevented from reaching a detection region where an antigen-antibody reaction occurs.

The present inventors have found that a material that is a woven fabric having a basis weight of 10 to 400 g/m² and a thickness of 0.1 to 2.0 mm, is highly absorbable, is highly water-retainable, and is capable of continuously releasing a neutralizing agent for a long period of time (1 hour or longer) is used as a porous material in a region impregnated with a neutralizing reagent, and by using such a material, a sufficient neutralizing ability can be maintained even when an acid is developed in small portions to a downstream portion of a test strip after a lapse of a given period of time (e.g., at or after 5 minutes which is the time of judgment), so that a non-specific reaction is suppressed. The present inventors have further found that in the case of using a highly absorbable and water-retainable and low releasable glass filter, an acid impregnated into a sample pad moves to a neutralization pad after a lapse of a given period of time, and is then released from the region and thus prevented from reaching a detection region where an antigen-antibody reaction occurs, so that a non-specific reaction is suppressed in a negative case, and color development of a line is prevented at or after the time of judgment in a positive specimen at or around the minimum detection sensitivity, thereby completing the present invention.

Specifically, the present invention includes the following aspects.

[1] An immunochromatographic test piece for extracting and measuring a sugar chain antigen in a specimen, the immunochromatographic test piece comprising: a sample pad to which a specimen mixed with nitrite or an acid solution is added; a label region comprising a labeled antibody obtained by labeling an antibody against the sugar chain antigen; and a detection region on which the antibody against the sugar chain antigen is immobilized, wherein an antibody-sugar chain antigen-labeled antibody complex is formed in the detection region to measure the sugar chain antigen, and the immunochromatographic test piece having a region impregnated with a neutralizing reagent upstream of the label region, and further having a region impregnated with a solid acid reagent when the specimen mixed with the nitrite is used, or a region impregnated with nitrite when the specimen mixed with the acid solution is used, upstream of the region impregnated with the neutralizing reagent, wherein
  a material for the region impregnated with the neutralizing reagent is a filter or a glass filter having three properties of being highly absorbable, being highly water-retainable, and being low releasable or continuously releasable, and
  owing to the high water-absorbable property and the high water-retainable property of the region impregnated with the neutralizing reagent, the acid solution containing the sugar chain antigen is sufficiently neutralized, and owing to the low releasable property or the sustained releasable property of the region impregnated with the neutralizing reagent, a remaining acid solution is prevented from arriving at the detection region, or a sufficiently neutralized test solution is continuously developed to the detection region, so that a non-specific reaction is suppressed.

[2] An immunochromatographic test piece for extracting and measuring a sugar chain antigen in a specimen, the immunochromatographic test piece comprising: a sample pad to which a specimen mixed with nitrite or an acid solution is added; a label region comprising a labeled antibody obtained by labeling an antibody against the sugar chain antigen; and a detection region on which the antibody against the sugar chain antigen is immobilized, wherein an antibody-sugar chain antigen-labeled antibody complex is formed in the detection region to measure the sugar chain antigen, and the immunochromatographic test piece having a region impregnated with a neutralizing reagent upstream of the label region, and further having a region impregnated with a solid acid reagent when the specimen mixed with the nitrite is used, or a region impregnated with nitrite when the specimen mixed with the acid solution is used, upstream of the region impregnated with the neutralizing reagent, wherein
  a material for the region impregnated with the neutralizing reagent is a woven fabric having a basis weight of 10 to 400 g/m$^2$ and a thickness of 0.1 to 2.0 mm.

[3] The immunochromatographic test piece according to the above [1] or [2], wherein the woven fabric absorbs water in an amount of 10 to 100 µl/cm$^2$ per cm/m$^2$, has a water absorption speed of 1.0 to 5.0 µl/sec, retains water in an amount of 10 to 100 µl/cm$^2$ after a fragment of 1 cm/m$^2$ is allowed to come in a wet state into contact with the detection region and left standing for 5 minutes, and has a liquid spread area of 20 mm$^2$ or smaller after a fragment of 1 cm/m$^2$ is allowed to come in a wet state into contact with a membrane and left standing for 5 minutes.

[4] The immunochromatographic test piece according to any one of the above [1] to [3], wherein owing to the high water-absorbable property and the high water-retainable property of the region impregnated with the neutralizing reagent, the acid solution containing the sugar chain antigen is sufficiently neutralized, and owing to the sustained releasable property of the region impregnated with the neutralizing reagent, a sufficient neutralizing ability is maintained even when a remaining acid solution arrives at the detection region, so that a non-specific reaction is suppressed.

[5] The immunochromatographic test piece according to any one of the above [1] to [4], wherein owing to the high water-absorbable property and the high water-retainable property of the region impregnated with the neutralizing reagent, the acid solution containing the sugar chain antigen is sufficiently neutralized, and owing to the low releasable property of the region impregnated with the neutralizing reagent, a remaining acid solution is prevented from arriving at the detection region, so that a non-specific reaction is suppressed in a negative case, and color development of a line is prevented at or after the time of judgment in a positive case.

[6] The immunochromatographic test piece according to any one of the above [1] to [5], wherein the region impregnated with the solid acid reagent or the nitrite is present on the sample pad or on the pad with the label region applied thereto.

[7] The immunochromatographic test piece according to any one of the above [1] to [6], wherein the solid acid reagent is selected from the group consisting of malonic acid, malic acid, maleic acid, citric acid, and tartaric acid.

[8] The immunochromatographic test piece according to any one of the above [1] to [7], wherein the neutralizing reagent is tris(hydroxymethyl)aminomethane or sodium hydroxide.

[9] The immunochromatographic test piece according to any one of the above [1] to [8], wherein the sugar chain antigen is the sugar chain antigen of protozoa, fungi, bacteria, *Mycoplasma, Rickettsia, Chlamydia*, or virus.

[10] A method of measuring a sugar chain antigen in a specimen according to an immunochromatography method using the immunochromatographic test piece according to any one of the above [1] to [9],
  the method comprising
mixing the specimen with a nitrous acid solution when the immunochromatographic test piece has a region impregnated with a solid acid reagent, or mixing the specimen with an acid solution when the immunochromatographic test piece has a region impregnated with nitrite, and adding the mixture to a sample pad of the immunochromatographic test piece, wherein in the immunochromatography method,
  the sugar chain antigen is extracted from the specimen by the action of nitrous acid generated through a reaction of the nitrite with the solid acid reagent in the region impregnated with the solid acid reagent or the region impregnated with the nitrite, the acid solution containing the sugar chain antigen is neutralized in a region impregnated with a neutralizing reagent, and an antibody-sugar chain antigen-labeled antibody complex is formed in a detection region, and wherein
owing to the high water-absorbable property and the high water-retainable property of the region impregnated with the neutralizing reagent, the acid solution containing the sugar chain antigen is sufficiently neutralized, and owing to the low releasable property or the sustained releasable property of the region impregnated with the neutralizing reagent, a remaining acid solution is prevented from arriving at the detection region, or a sufficiently neutralized test solution is continuously developed to the detection region, so that a non-specific reaction is suppressed.

The present description includes the contents as disclosed in Japanese Patent Application No. 2017-049155, which is a priority document of the present application.

Advantageous Effects of Invention

In the immunochromatographic test piece of the present invention for measuring an antigen of group A β-hemolytic *Streptococcus*, which is capable of extracting a sugar chain antigen with nitrous acid on the immunochromatographic test piece, a pad, in which a material having three properties of being highly water-absorbable, being highly water-retainable (liquid-retainable), and being low liquid-releasable or continuously liquid-releasable is impregnated with a neutralizing reagent, is disposed at a position downstream of an antigen extraction site and upstream of a labeling site. By this structure, a non-specific reaction after a lapse of time can be suppressed.

Figure 1:
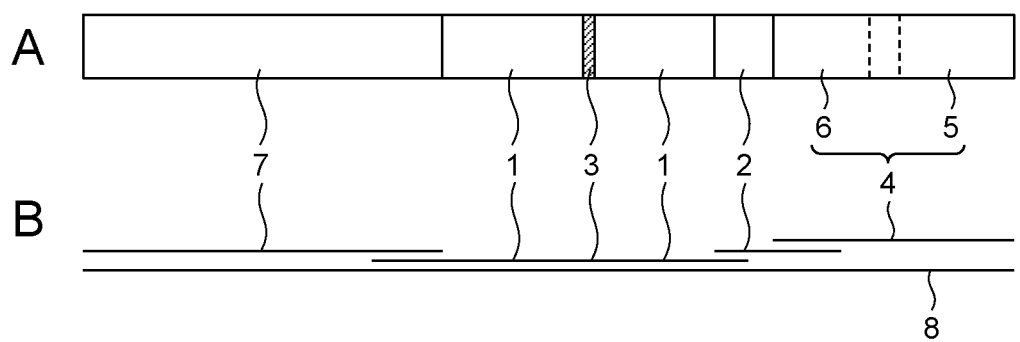
FIG. 1 is a view schematically showing a structure of an immunochromatographic test piece (one-pad test piece) having a solid acid reagent region and a neutralizing reagent region.

Hereinafter, the present invention will be described in detail.

The present invention relates to an immunochromatographic test piece which simplifies a treatment of extracting a sugar chain antigen with nitrous acid on an immunochromatographic test piece, so that the sugar chain antigen used as a substance to be detected can be measured promptly and accurately.

The immunochromatographic test piece comprises a support having a detection region, on which an antibody (Antibody 1) that captures a substance to be detected (antigen, etc.) is immobilized, a label region having a movable labeled antibody (Antibody 2), a sample pad to which a specimen is added, an absorption band that absorbs a developed specimen solution, a backing sheet for adhering these members to one another, and the like.

The immunochromatographic test piece of the present invention may be accommodated in a storing container. Such a storing container can prevent the degradation of the test piece, which is caused by, for example, ultraviolet ray or moisture contained in the air. Moreover, in the case of treating a specimen or a sample having contamination or infectivity, such a storing container can prevent a tester performing an assay from being contaminated or infected with the specimen or the sample. For instance, a resin-made case having a suitable size may be used as a storing container, and the device of the present invention may be accommodated in the case. Otherwise, the surface of a test piece, on which an antigen or an antibody has been immobilized, may be coated with a resin-made film or the like (top laminate). There is a case where a storing container and a test piece accommodated in the storing container are collectively referred to as an immunochromatographic device.

It is to be noted that the number of detection regions and the type of a labeled antibody contained in the label region are not limited to one, and that, by using antibodies corresponding to a plurality of substances to be detected, two or more antigens can be measured on a single test piece.

The support is a material having the property of immobilizing an antibody used to capture a substance to be detected (an antigen), and also, it does not prevent the movement of a liquid in the horizontal direction. Preferably, the support is a porous thin membrane (a membrane) having capillary action, and is a material capable of transporting a liquid and components dispersed in the liquid according to absorption. The material used for the support is not particularly limited, and examples of the material include cellulose, nitrocellulose, cellulose acetate, polyvinylidene difluoride (PVDF), glass fiber, nylon, and polyketone. Among these materials, a thin membrane or a membrane of nitrocellulose is more preferable. A membrane, on which an antibody is immobilized, is referred to as an "antibody-immobilized membrane."

The label region consists of a porous substrate comprising a labeled antibody, and a commonly used glass fiber, non-woven fabric, and the like can be used herein as a material for the substrate. The substrate is preferably a pad having a thickness of approximately 0.3 mm to 0.6 mm, in order that the substrate is impregnated with a large amount of labeled antibody. A porous substrate that is impregnated with a labeled antibody and is then dried is also referred to as a dry pad.

For the labeling of a labeled antibody, enzymes such as alkaline phosphatase or horse radish peroxidase, metal colloids such as gold colloids, silica particles, cellulose particles, colored polystyrene particles, colored latex particles, etc. are used in many cases. When metal colloidal particles or colored particles such as colored polystyrene particles or colored latex particles are used, color is developed by clumping of these labeling reagents. So, the thus developed color is measured. Particles, on which antibodies are immobilized, are referred to as antibody-immobilized particles.

The detection region indicates a region of the support, on which an antibody used to capture a substance to be detected (an antigen) is immobilized. In the detection region, at least one region, on which an antibody used to capture an antigen is immobilized, is established. The detection region may be comprised in the support, and an antibody may be immobilized on the support.

The sample pad is a site to which a specimen is added, and is a porous material. The sample pad is a site located most upstream of the immunochromatographic test piece. As a material for the sample pad, a commonly used filter, glass fiber, non-woven fabric, etc. can be used. In order to use a large amount of specimen in immunoassay, the sample pad is preferably a pad having a thickness of approximately 0.3 mm to 1 mm. The specimen also includes a sample prepared using the specimen, such as a sample obtained by suspending the specimen in another solution.

The absorption band is a member for absorbing components, which are supplied to the support and are not associated with the reaction in the detection region. As a material for the absorption band, a highly water-retainable filter, sponge or the like, consisting of a common natural high-molecular-weight compound, synthetic high-molecular-weight compound, etc. can be used. In order to promote the development of a specimen, highly water-absorbable material is preferably used as an absorption band.

The backing sheet is a member used for adhesion and/or immobilization of all of the aforementioned materials, namely, the support, the sample pad, the label region, the absorption band and the like, in which these materials are partially overlapped with one another. The backing sheet is not necessarily required, if these materials are arranged and immobilized with optimal intervals. However, in general, the backing sheet is preferably used for convenience or ease of production or use.

In the immunochromatographic test piece of the present invention, a control display region (a member) may be further present. The control display region is a site showing that a test is accurately carried out. For example, the control display region is located downstream of the detection region, and emits signals such as coloration, when a specimen sample is passed through the detection region and reaches the control display region. On the control display region, a substance binding to a labeled carrier-bound antibody may be solid-phased, or a reagent such as a pH indicator, the color of which is changed when a specimen reaches, may also be solid-phased. When such a labeled carrier-bound antibody is a mouse monoclonal antibody, an anti-mouse IgG antibody may be used.

The size of an immunochromatographic test piece is not limited. For example, the height thereof is from several cm to more than ten and less than 20 cm, and the width thereof is from approximately several mm to several cm.

In the test piece having the above-described form, the specimen is passed through a porous flow channel formed by connecting a series of members, such as the sample pad, the label region, the support, the detection region, the absorption band and the like, with one another. Accordingly, in the present embodiment, all of these components constitute a specimen moving region. There may also be an embodiment, in which the specimen does not penetrate into various constitutional materials but pass through the interface, depending on the materials or forms of the constitutional materials. However, since the specimen moving region defined in the present description is irrelevant to whether the specimen passes into the material or passes through the interface, the test piece having the aforementioned embodiment is also included in the scope of the present description.

In the case of measuring a sugar chain antigen in a specimen using the immunochromatographic test piece of the present invention, it is necessary to first extract the sugar chain antigen in the specimen. The extraction of the sugar chain antigen is performed by treating the specimen containing the sugar chain antigen with nitrous acid. The nitrous acid can be generated by mixing nitrite such as sodium nitrite with an acid, and the specimen containing the sugar chain antigen may be treated with the nitrous acid thus generated. The extracted antigen binds through an antigen-antibody reaction to the antibody immobilized on the immunochromatographic test piece. In this respect, the reaction system becomes strongly acidic if nitrous acid remains in the reaction system, so that the antigen-antibody reaction is inhibited. Thus, it is necessary to neutralize nitrous acid in the reaction system.

In the method of measuring a sugar chain antigen by mixing nitrite with an acid to generate nitrous acid, extracting the sugar chain antigen from a specimen with the nitrous acid, neutralizing the nitrous acid, and then allowing the sugar chain antigen to bind to the antibody immobilized on the immunochromatographic test piece, according to the present invention, examples of the method of extracting and measuring the sugar chain antigen include the following methods. In any of the methods, the extraction of the sugar chain antigen with nitrous acid, and the neutralization are performed on the immunochromatographic test piece. In order to perform the extraction of the sugar chain antigen with nitrous acid on the immunochromatographic test piece, the immunochromatographic test piece can be impregnated with an acid reagent or nitrite. In order to perform the neutralization on the immunochromatographic test piece, the immunochromatographic test piece can be impregnated with a neutralizing reagent.

(A) A specimen is previously mixed with an acid solution, and the mixture is added to a sample pad of the immunochromatographic test piece impregnated with nitrite and a neutralizing reagent. When the mixed solution arrives at the region impregnated with the nitrite, the nitrite reacts with the acid to generate nitrous acid, so that a sugar chain antigen in the specimen is extracted. The extract of the sugar chain antigen is neutralized in the region impregnated with the neutralizing reagent on the immunochromatographic test piece, and the sugar chain antigen binds to the antibody immobilized on the immunochromatographic test piece and can thus be detected. In this method, examples of the acid solution used include acetic acid, hydrochloric acid, malonic acid, malic acid, maleic acid, citric acid, and tartaric acid.

(B) A specimen is previously mixed with a nitrite solution, and the mixture is added to a sample pad of the immunochromatographic test piece impregnated with an acid reagent and a neutralizing reagent. When the mixed solution arrives at the region impregnated with the acid reagent, the nitrite reacts with the acid to generate nitrous acid, so that a sugar chain antigen in the specimen is extracted. The extract of the sugar chain antigen is neutralized in the region impregnated with the neutralizing reagent on the neutralizing immunochromatographic test piece, and the sugar chain antigen binds to the antibody immobilized on the immunochromatographic test piece and can thus be detected.

In the immunochromatographic test piece of the present invention for performing the above-described method (A) or (B), the acid reagent or the nitrate and the neutralizing reagent are impregnated upstream of the label region (on the upstream side along the flow of the specimen, where the sample pad is present), namely, within the sample pad or between the sample pad and the label region. The immunochromatographic test piece, in which the nitrite and the neutralizing reagent are impregnated within the sample pad or between the sample pad and the label region, can be used in the above-described method (A). Also, the immunochromatographic test piece, in which the acid reagent and the neutralizing reagent are impregnated within the sample pad or between the sample pad and the label region, can be used in the above-described method (B). It is to be noted that as the acid reagent, a solid acid reagent is used. According to these methods, a substance to be detected in a test sample can be measured accurately and specifically, regardless of the amount of the test sample subjected to a test.

The solid acid reagent or the nitrite may be impregnated into the sample pad, or may be impregnated into a pad made of a porous material that is different from the sample pad, such as a non-woven fabric, and the obtained solid acid reagent-impregnated porous material or nitrite-impregnated porous material may be disposed between the sample pad and the label region, namely, on the side upstream of the label region. Herein, the region impregnated with the solid acid reagent or the nitrite may be contacted or may not be contacted with the sample pad or the label region.

In the present invention, the region impregnated with a reagent is also referred to as a pad impregnated with a reagent.

The neutralizing reagent is disposed downstream of the region impregnated with the solid acid reagent or the nitrite. The neutralizing reagent may be impregnated into the sample pad, or may be impregnated into the support, or may be impregnated into a pad made of a porous material that is different from the support, such as a non-woven fabric (such as nylon) and a fabric, and the obtained neutralizing reagent-impregnated porous material may be disposed between the region impregnated with the solid acid reagent or the nitrite and the label region. That is, the immunochromatographic test piece has a region impregnated with a neutralizing reagent upstream of the label region, and further has a region impregnated with a solid acid reagent or nitrite upstream of the region impregnated with the neutralizing reagent.

Examples of the porous material to be used in the region impregnated with the neutralizing reagent include a porous material that is a woven fabric having a basis weight of 10 to 400 g/m² and a thickness of 0.1 to 2.0 mm, absorbs water in an amount of 10 to 100 µl/cm² per cm/m², has a water absorption speed of 1.0 to 5.0 µl/sec, retains water in an amount of 10 to 100 µl/cm² after a fragment of 1 cm/m² is allowed to come in a wet state into contact with a membrane and left standing for 5 minutes, and preferably has a liquid spread area of 20 mm² or smaller after a fragment of 1 cm/m² is allowed to come in a wet state into contact with a membrane and left standing for 5 minutes, namely has three properties of being highly water-absorbable, being highly water-retainable (liquid-retainable), and being low liquid-releasable or continuously liquid-releasable. Specific examples thereof include a filter made of cellulose cotton fiber, and a glass filter made of glass fiber. Examples of such a filter include No. 26-3 from Toyo Roshi Kaisha, Ltd. Moreover, the filter to be used has a large capacity and can sufficiently retain an acid solution that reaches the filter later than a specimen from the upstream portion. By using such a porous material, the neutralizing reagent can be impregnated thereinto in an amount that can sufficiently neutralize a specimen from which a sugar chain antigen has been extracted with nitrous acid generated through a reaction of nitrite with the acid reagent. Moreover, the pad can absorb and retain a large amount of liquid and sustains the releasable property. Hence, if a liquid containing nitrous acid remaining upstream of the immunochromatographic test piece is developed at or after the time of judgment, the pad can have a sufficient neutralizing ability and can prevent the acid solution from arriving at the detection region on which the antibody is immobilized. As a result, a non-specific reaction is suppressed, and the sugar chain antigen can be detected without causing the non-specific reaction. On the other hand, specific examples of the highly water-absorbable, highly water-retainable, and low releasable glass filter include GS-25 from Toyo Roshi Kaisha, Ltd. which can be impregnated with a larger amount of neutralizing reagent because of the high water-absorbable property, and prevents the acid solution from arriving at the immobilized detection region because of the high water-retainable property and the low water-releasable property. As a result, a non-specific reaction can be suppressed in a negative case, and color development of a line can be prevented at or after the time of judgment in a positive case.

The "basis weight" of the porous material to be used in the region impregnated with the neutralizing reagent is 10 to 400 g/m². Herein, the "basis weight" indicates a weight per unit area (1 m²) of a fabric or the like. The basis weight can be appropriately changed by adjusting the amount or composition of the neutralizing reagent impregnated into the pad. If the basis weight is 30 g/m² or less, the porous material has a high porosity and is easily torn when impregnated with the neutralizing reagent, and is thus difficult to handle during immunochromatographic production. Hence, the basis weight is preferably 50 g/m² or more. If the basis weight is 300 g/m² or more, the porous material has a low porosity and does not permit smooth penetration of a specimen into the material, albeit depending on the composition of the neutralizing reagent, so that the specimen cannot be mixed with the neutralizing reagent. Hence, the basis weight is preferably 300 g/m² or less. The basis weight is most preferably 250 to 270 g/m².

The "thickness" of the porous material to be used in the region impregnated with the neutralizing reagent is preferably 0.1 to 2.0 mm. The thickness can be appropriately changed by adjusting the amount or composition of the neutralizing reagent impregnated into the pad. If the thickness is 0.4 mm or less, the porous material is easily torn when impregnated with the neutralizing reagent, and is thus difficult to handle during immunochromatographic production. Hence, the thickness is preferably 0.4 to 0.8 mm and is more preferably approximately 0.6 mm in consideration of the easiness with which the amount of the neutralizing reagent impregnated is adjusted, and the easiness of handling during immunochromatographic production.

The "water-absorbable" property is preferably 10 to 100 µl/cm² in terms of an amount of water absorbed per cm/m², and 1.0 to 5.0 µl/sec in terms of a water absorption speed. The amount of water absorbed and the water absorption speed are determined by preparing 200 µl of a colored solution (1% Tween 20+Red No. 102) in one cell of a 96-well EIA plate, placing therein a test piece, in which a material having a size of 5×60 mm adheres to a backing sheet, measuring the time for the solution to arrive at the upper end of the test piece (an end of the test piece dipped in the solution is defined as a lower end), further taking the test piece out of the solution immediately after the solution reaches the upper end, and measuring the amount of a liquid remaining in the cell. The amount of water absorbed is the amount of a liquid calculated by subtracting the amount of the liquid remaining in the cell from 200 and dividing the obtained value by 1 cm² of the area of the material. The water absorption speed is determined according to the amount of water absorbed/the time required to reach the upper end. The porous material to be used in the region impregnated with the neutralizing reagent is preferably a material having a larger amount of water absorbed and a slower water absorption speed. If the amount of water absorbed is 30 µl/cm² or less, albeit depending on the concentration and water content of the solid acid reagent, it is considered that the amount of the neutralizing reagent impregnated may fall short of an amount necessary for the immunochromatographic test piece. Specifically, the amount of water absorbed is preferably 30 µl/cm² or more. The water absorption speed of the porous material to be used in the region impregnated with the neutralizing reagent influences the time required to extract a sugar chain antigen from a specimen, and the time required to neutralize a test solution after the extraction. The time required to extract a sugar chain antigen can be adjusted to some extent, but not completely, by adjusting the material or composition of the solid acid reagent. Hence, the water absorption speed of the porous material to be used in the region impregnated with the neutralizing reagent is an important factor for sufficient extraction of the sugar chain antigen and neutralization. Specifically, the water absorption speed is preferably 1.0 to 5.0 µl/sec. The water absorption speed is more preferably 2.0 µl/sec or less.

The "water-retainable" property is determined by placing, on a membrane, a fragment of 1 cm/m² obtained from the porous material to be used in the region impregnated with the neutralizing reagent, adding thereto 70 µl of a solution (1% Tween 20+Red No. 102), and measuring the weight of the membrane before and after the membrane is left standing for 5 minutes. The amount of a liquid for the water-retainable property varies depending on the composition (a surfactant or a protein) of the solution to be added. In the case of a test using a 1% Tween 20 solution, the amount of water retained is preferably 10 to 100 µl/cm². The amount of water retained is more preferably 15 µl/cm² or more.

The "releasable" property is measured by placing, on a membrane, a fragment of 1 cm/m² obtained from the porous material to be used in the region impregnated with the neutralizing reagent, adding thereto 70 µl of a solution (1% Tween 20+Red No. 102), and determining the area of a liquid spread on the membrane after the membrane is left standing for 5 minutes. The area varies depending on the composition (a surfactant or a protein) of the solution to be added. In the case of a test using a 1% Tween 20 solution, the area is 30 mm² or less. The releasable property is more preferably 20 mm² or less as this area.

Here, the region impregnated with the neutralizing reagent, and the region impregnated with the solid acid reagent or nitrite or the label region may or may not be in contact with each other.

The region impregnated with the solid acid reagent is referred to as a solid acid reagent region, the region impregnated with the nitrite is referred to as a nitrite region, and the region impregnated with the neutralizing reagent is referred to as a neutralizing reagent region or a basic reagent region.

The immunochromatographic test piece having a solid acid reagent region or a nitrite region and a neutralizing reagent region has, on the support, a sample pad, a solid acid reagent region or a nitrite region, a neutralizing reagent region, a label region, a detection region, and an absorption band, from the upstream thereof, and the solid acid reagent region or the nitrite region may be located on the sample pad. Moreover, the sample pad, the solid acid reagent region or the nitrite region, the neutralizing reagent region, the label region, the detection region, and the absorption band may be contacted or may not be contacted with a region adjacent thereto. Furthermore, the solid acid reagent region or the nitrite region, the neutralizing reagent region, and the label region are not necessarily impregnated into each different porous material, and a plurality of or all of the regions may be impregnated into a single porous material.

The solid acid reagent used in the present invention is in a solid state at normal temperature and does not volatilize at a high temperature.

Examples of the solid acid reagent that is preferably used in the present invention can include malonic acid, malic acid, maleic acid, citric acid, and tartaric acid.

If an acid with a higher valence, for example, citric acid, is used as a preferred solid acid reagent in the present invention, extraction can be performed with a smaller amount of acid. On the other hand, if the valence of an acid is the same, for example, maleic acid or tartaric acid having a smaller acid dissociation constant is more efficient.

Also, the solid acid reagent used in the present invention is preferably a reagent that is not colored on the immunochromatographic test piece, and more specifically, a reagent, which has white color in a dry state or is hardly colored by dry heat or oxidation.

Examples of the nitrite used in the present invention include sodium nitrite and potassium nitrite.

The amount of the solid acid reagent or the nitrite used in the present invention, namely, the amount of the solid acid reagent or the nitrite impregnated into the immunochromatographic test piece is not particularly limited. In general, the amount of the solid acid reagent or the nitrite is approximately 0.01 µg to 1 mg, and is preferably approximately 0.1 µg to 0.1 mg, with respect to a single immunochromatographic test piece. However, it is preferable to select an optimal amount, in which effects can be obtained depending on the type of the solid acid reagent or the nitrite to be used, the composition of a specimen suspension, the amount added, etc.

In order to impregnate a sample pad or a porous material with the solid acid reagent or the nitrite, the solid acid reagent or the nitrite is once dissolved in a solution, and the obtained solution is then applied to the sample pad or the porous material and is then dried.

The neutralizing reagent used in the present invention is in a solid state at normal temperature and does not volatilize at a high temperature.

Examples of the neutralizing reagent that is preferably used in the present invention include Tris base (tris(hydroxymethyl)aminomethane), sodium hydroxide, dipotassium hydrogen phosphate, trisodium citrate, and a Good's buffer having a buffering ability in the alkaline range.

The amount of the neutralizing reagent used in the present invention, namely, the amount of the neutralizing reagent impregnated into the immunochromatographic test piece is not particularly limited. In general, the neutralizing reagent is used in an amount of approximately 0.01 µg to 1 mg, and preferably approximately 0.1 µg to 0.1 mg, for a single immunochromatographic test piece. However, it is preferable to select an optimal amount, in which effects can be obtained depending on the type of the used neutralizing reagent, the composition of a specimen suspension, the amount added, etc.

In order to impregnate a sample pad or a porous material with the neutralizing reagent, the neutralizing reagent may be once dissolved in a solution, the obtained solution may be then applied to the sample pad or the porous material, and thereafter, it may be dried.

Figure 2:
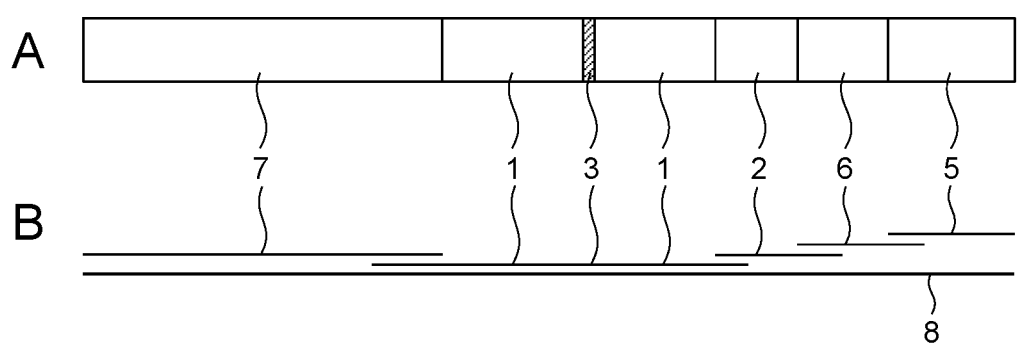
FIG. 2 is a view schematically showing a structure of an immunochromatographic test piece (two-pad test piece) having a solid acid reagent region and a neutralizing reagent region.

FIG. 1 and FIG. 2 are views each showing a preferred embodiment of a typical immunochromatographic test piece. The immunochromatographic test piece shown in FIG. 1 or FIG. 2 is an immunochromatographic test piece impregnated with a solid acid reagent and a neutralizing reagent. However, nitrate may be impregnated instead of the solid acid reagent, and the resultant is an immunochromatographic test piece impregnated with nitrate and a neutralizing reagent. Those skilled in the art can appropriately design and produce an immunochromatographic test piece impregnated with nitrate and a neutralizing reagent. It is to be noted that the immunochromatographic test piece is not limited to those shown in FIG. 1 and FIG. 2. In FIG. 1 and FIG. 2, reference numeral 1 denotes a support, reference numeral 2 denotes a label region, reference numeral 3 denotes a detection region, reference numeral 4 denotes a sample pad, reference numeral 7 denotes an absorption band, and reference numeral 8 denotes a backing sheet. Moreover, a top laminate may adhere onto the entire test piece.

FIG. 1A and FIG. 2A are top views, and FIG. 1B and FIG. 2B are cross-sectional views. In the example shown in FIG. 1, a support 1 on which one detection region 3 is formed, an absorption band 7, a label region 2, a sample pad 4, and the like, are laminated on a backing sheet 8 made of resin or the like. As shown in FIG. 1, one end of the absorption band 7 is laminated on one end of the support 1, the other end of the support 1 is laminated on one end of the label region 2, and the other end of the label region 2 is laminated on one end of the sample pad 4. A portion upstream of the sample pad 4 is impregnated with a solid acid reagent, and a portion downstream of the sample pad is impregnated with a neutralizing reagent, which is somewhat apart from the upstream portion. The region impregnated with the solid acid reagent is referred to as a solid acid reagent region 5, and the region impregnated with the neutralizing reagent is referred to as a neutralizing reagent region 6. In this test piece, the sample pad also serves as a solid acid reagent region 5 and a neutralizing reagent region 6. That is, the solid acid reagent region and the neutralizing reagent region are present on the sample pad. This test piece, in which the solid acid reagent region and the neutralizing reagent region are established as one porous material (pad), is also referred to as a one-pad test piece. In the example shown in FIG. 2, the solid acid reagent region 5 and/or the neutralizing reagent region 6 is present upstream of the label region 2, and these are overlapped with each other, so that a flow channel of a continuous lateral flow is formed. In the test piece shown in FIG. 2, the solid acid reagent region 5 also serves as a sample pad. That is, the solid acid reagent region is present on the sample pad. In this test piece, in which the solid acid reagent region and the neutralizing reagent region are established as two different porous materials (pads), is also referred to as a two-pad test piece. A sample pad may further be present upstream of the solid acid reagent region. In the test piece shown in FIG. 2, the solid acid reagent region 5 and the neutralizing reagent region 6 are impregnated into different porous materials. However, on a single porous material (pad), the solid acid reagent region 5 is established in an upstream portion, and the neutralizing reagent region 6 is established in a downstream portion, as in the sample pad of the test piece shown in FIG. 1.

A method of using the test piece of the present invention will be described on the basis of the form shown in FIG. 1. The following use method is a method of mixing a specimen with a nitrous acid solution and carrying out measurement by use of an immunochromatography method, in which a solid acid reagent and a neutralizing reagent are impregnated. A method of mixing a specimen with an acid solution and carrying out measurement by use of an immunochromatography testing method, in which nitrite and a neutralizing reagent are impregnated, can also be performed with reference to the description of the following use method.

A specimen or a sample prepared using the specimen is contacted and mixed with a nitrite solution, and the specimen is suspended in the nitrite solution, and the suspension is then added to the specimen addition port of the device, so that the measurement is initiated. This time, 5 to 100 µL of a specimen may be mixed with 0.01 to 2 mL of 0.1 M to 8 M nitrite, and 5 to 200 µL of the mixture may be then added to the addition port. Examples of the nitrite include sodium nitrite and potassium nitrite.

A specimen containing a sugar chain antigen as a substance to be detected, which is subjected to a sample pad 4, is developed to a solid acid reagent region 5 and a neutralizing reagent region 6 on the sample pad 4 according to capillary action, and further, is successively developed to a label region 2, a support 1, and an absorption band 7 in the horizontal direction. In the solid acid reagent region 5, nitrite mixed with the specimen reacts with a solid acid reagent on the solid acid reagent region 5 to generate free nitrous acid, so that a sugar chain antigen is extracted from the specimen by the action of the nitrous acid. The extracted sugar chain antigen is developed and moved, together with an acidic developing solution, to the neutralizing reagent region 6, and the pH of the acidic developing solution containing the sugar chain antigen is neutralized at the neutralizing reagent region 6, so that it is adjusted to the neutral range. As a result, the sugar chain antigen is further developed and moved to the downstream region under neutral conditions. In the label region 2, with the development of a specimen sample, a labeled antibody is released into the liquid, and it is then developed to the support 1. When a sugar chain antigen is present in a specimen sample, the sugar chain antigen is specifically captured by a capturing antibody at a detection region 3 in the support 1, and the sugar chain antigen also has a specific reaction with a labeled antibody to form a complex. Thereby, at the detection region 3, the sandwiching of the antibody via the sugar chain antigen is achieved, so that a labeled antibody-sugar chain antigen complex can be measured at the detection region 3.

According to the method using the immunochromatographic test piece of the present invention, since the extraction of a sugar chain antigen from a specimen is carried out on the immunochromatographic test piece, it is not necessary to previously extract the sugar chain antigen from the specimen before the measurement using the immunochromatographic test piece, but the sugar chain antigen in the specimen can be measured by a single step.

In the method of the present invention, a biological sample used as a specimen is not particularly limited. Examples of such a biological sample include body fluid and the like such as serum, plasma, blood, urine, feces, saliva, tissue fluid, spinal fluid or swab, and a diluted product thereof.

In the method using an immunochromatographic device of the present invention, a substance to be detected as an analyte is a sugar chain antigen, which can be measured by an immunoassay, namely, an assay utilizing an antigen-antibody reaction. An example of the antigen is a polysaccharide that is a sugar chain antigen present on the cell wall of bacteria extracted by a nitrous acid extraction treatment. Protozoa, fungi, bacteria, *Mycoplasma, Rickettsia, Chlamydia*, virus, and others comprising the aforementioned substance can also be measured. According to the method using an immunochromatographic test piece of the present invention, whether or not a sugar chain antigen derived from protozoa, fungi, bacteria, *Mycoplasma, Rickettsia, Chlamydia*, virus, etc. is contained in the biological sample of a subject can be confirmed. When such a sugar chain antigen is contained in the biological sample, it can be determined that the subject is affected with infection caused by the protozoa, fungi, bacteria, *Mycoplasma, Rickettsia, Chlamydia*, virus, etc. For example, group A β-hemolytic *Streptococcus* (*Streptococcus pyogenes*), the presence or absence of infection with *Escherichia coli, Legionella, Campylobacter*, etc. can be detected.

In order to allow a specimen from which a sugar chain antigen has been extracted with nitrous acid generated through a reaction of nitrite with an acid, to be absorbed to a pad impregnated with a neutralizing reagent and to stay in the pad long enough to reliably neutralize the specimen, a member as a replacement for a filter or a glass filter, which has physical characteristics and properties for controlling the development of a specimen sample solution on the immunochromatographic test piece, may be established upstream of a labeling site. That is, in the present invention, the porous material to be used in the region impregnated with the neutralizing reagent may be pretreated according to the need. In order to control the degree of hydrophilicity or the degree of hydrophobicity, a material having physical characteristics or properties other than those mentioned above may be processed into the range of the physical characteristics or the properties described in the present invention by allowing the neutralizing reagent to contain various drugs or powders. Examples of the drug to be contained include surfactants, proteins, resins, and chemically synthesized polymers. Examples of the member that may be provided with features similar to those of a filter or a glass filter include non-woven fabrics such as nylon.

In the present invention, when the solid acid reagent region or the nitrite region and the neutralizing reagent region are overlapped and contacted with each other, a sheet impermeable to a liquid is established such that the sheet is sandwiched between the solid acid reagent region or the nitrite region and the neutralizing reagent region. The establishment of the sheet can produce the following three effects.

(A) The movement of a reagent between two adjacent regions can be suppressed during preservation of the test piece. As a result, the reaction of a solid acid reagent or nitrite with a neutralizing reagent by contact can be prevented. As a result, the stability of the reagent can be improved.

(B) When a specimen mixed with nitrite or an acid reagent is added, insufficient extraction of a sugar chain antigen ascribable to the specimen that reaches the solid acid reagent region or the nitrite region and immediately thereafter moves to the neutralizing reagent region can be prevented. That is, the rate at which a liquid containing the specimen moves from the solid acid reagent region or the nitrite region to the neutralizing reagent region is decreased, and the time for which the liquid containing the specimen stays in the solid acid reagent region or the nitrite region is lengthened. As a result, a sugar chain antigen is sufficiently extracted, and measurement sensitivity is enhanced.

(C) When a specimen mixed with nitrite or an acid reagent is added, a liquid containing the specimen that has reached the solid acid reagent region or the nitrite region and immediately thereafter moved to the neutralizing reagent region can be prevented from flowing backward to the solid acid reagent region or the nitrite region, reducing the activity of the solid acid reagent or the nitrite, and reducing extraction efficiency. That is, a liquid containing the specimen that has once reached the neutralizing reagent region is prevented from flowing backward to the solid acid reagent region or the nitrite region and prevented from reducing the activity of the solid acid reagent or the nitrite. Thus, the extraction of the sugar chain antigen with nitrous acid is allowed to proceed efficiently, and measurement sensitivity is enhanced.

The material for the sheet to be established between the solid acid reagent region or the nitrite region and the neutralizing reagent region is not limited as long as the material is impermeable to a liquid. For example, a resin-made sheet such as a PET (polyethylene terephthalate) sheet or a polyethylene sheet can be used. The resin-made sheet is also referred to as a resin-made film.

The sheet may be established such that the solid acid reagent region or the nitrite region and the neutralizing reagent region are partially contacted and overlapped with each other. In this case, the length of the overlapped portion between the solid acid reagent region or the nitrite region and the neutralizing reagent region is preferably minimized and is, for example, 5 mm or less, preferably 3 mm or less, more preferably 2 mm or less.

The sheet may be established so as not to allow the solid acid reagent region or the nitrite region and the neutralizing reagent region into contact with each other, and the pad impregnated with the acid reagent or the nitrite may have a shape overhanging a PET sheet. In this case, the neutralization region may be completely coated with the sheet, and the solid acid reagent region or the nitrous acid region may be established on the sheet. In this case, a liquid within the solid acid reagent region or the nitrous acid region flows on the sheet without moving directly to the neutralization region, and then arrives at the neutralizing reagent region.

The sheet may be established, for example, only between the solid acid reagent region or the nitrite region and the neutralizing reagent region. On the other hand, when the resin-made sheet adheres, as a top laminate sheet, to and covers the upper side of the immunochromatographic test piece, the top laminate sheet adheres to and covers the neutralizing reagent region, the label region, the support, the detection region, and the absorption band excluding the solid acid reagent region or the nitrous acid region and further excluding the sample pad when the solid acid reagent region or the nitrous acid region also serves as the sample pad. The solid acid reagent region or the nitrite region may adhere to the upper part of the top laminate sheet adhering to the upper part of the neutralizing reagent portion.

Specifically, the present invention includes the following aspects.

[1] An immunochromatographic test piece for extracting and measuring a sugar chain antigen in a specimen, the immunochromatographic test piece comprising: a sample pad to which a specimen mixed with nitrite or an acid solution is added; a label region comprising a labeled antibody obtained by labeling an antibody against the sugar chain antigen; and a detection region on which the antibody against the sugar chain antigen is immobilized, wherein an antibody-sugar chain antigen-labeled antibody complex is formed in the detection region to measure the sugar chain antigen, and the immunochromatographic test piece having a region impregnated with a neutralizing reagent upstream of the label region, and further having a region impregnated with a solid acid reagent when the specimen mixed with the nitrite is used, or a region impregnated with nitrite when the specimen mixed with the acid solution is used, upstream of the region impregnated with the neutralizing reagent, wherein
a resin-made sheet is sandwiched between the region impregnated with the solid acid reagent or the nitrite and the region impregnated with the neutralizing reagent so as to suppress the movement of a reagent or the movement of a specimen solution between the regions.

[2] The immunochromatographic test piece according to the above [1], wherein the region impregnated with the solid acid reagent or the nitrite is present on the sample pad.

[3] The immunochromatographic test piece according to the above [1] or [2], wherein the resin-made sheet is sandwiched such that the region impregnated with the solid acid reagent or the nitrite and the region impregnated with the neutralizing reagent come into partial contact with each other.

[4] The immunochromatographic test piece according to the above [1] or [2], wherein the resin-made sheet is sandwiched such that the region impregnated with the solid acid reagent or the nitrite and the region impregnated with the neutralizing reagent do not come into contact with each other.

[5] The immunochromatographic test piece according to any one of the above [2] to [4], wherein the region impregnated with the solid acid reagent or the nitrite is present in a most upstream sample pad on the immunochromatographic test piece, regions except for the sample pad are coated with a resin-made sheet, and the sample pad impregnated with the solid acid reagent or the nitrite is present above the resin-made sheet located above the region impregnated with the neutralizing reagent.

[6] The immunochromatographic test piece according to any one of the above [1] to [5], wherein the solid acid reagent is selected from the group consisting of malonic acid, malic acid, maleic acid, citric acid, and tartaric acid.

[7] The immunochromatographic test piece according to any one of the above [1] to [6], wherein the neutralizing reagent is tris(hydroxymethyl)aminomethane or sodium hydroxide.

[8] The immunochromatographic test piece according to any one of the above [1] to [7], wherein the sugar chain antigen is the sugar chain antigen of protozoa, fungi, bacteria, *Mycoplasma, Rickettsia, Chlamydia*, or virus.

[9] A method of measuring a sugar chain antigen in a specimen according to an immunochromatography method using the immunochromatographic test piece according to any one of the above [1] to [8], the method comprising mixing the specimen with a nitrous acid solution when the immunochromatographic test piece has a region impregnated with a solid acid reagent, or mixing the specimen with an acid solution when the immunochromatographic test piece has a region impregnated with nitrite, and adding the mixture to a sample pad of the immunochromatographic test piece, wherein in the immunochromatography method, the sugar chain antigen is extracted from the specimen by the action of nitrous acid generated through a reaction of the nitrite with the solid acid reagent in the region impregnated with the solid acid reagent or the region impregnated with the nitrite, the acid solution containing the sugar chain antigen is neutralized in a region impregnated with a neutralizing reagent, and an antibody-sugar chain antigen-labeled antibody complex is formed in a detection region, and wherein a speed or a direction of development of the specimen on the immunochromatographic test piece is controlled, so that a treatment with the acid reagent, the nitrite, and the neutralizing reagent is controlled.

In the immunochromatographic device of the present invention, a wide addition port can also be established.

For example, the addition port of a conventional immunochromatographic device (QuickNavi™-Strep A, Denka Seiken Co., Ltd.), in which an immunochromatographic test piece having a length of 5 to 9 cm, preferably 7 cm, and a width of 0.3 to 0.7 cm, preferably 0.5 cm, is stored, is established as a substantially rectangular addition port having a size of approximately 3.5 mm×approximately 5.5 mm (19.25 mm$^2$). The addition port of the immunochromatographic device of the present invention, in which the immunochromatographic test piece having the same size as above is stored, is established as a substantially rectangular addition port having a size of approximately 3.5 mm×approximately 11 mm (38.5 mm$^2$). Since the immunochromatographic device and the immunochromatographic test piece stored therein generally have similar sizes, an immunochromatographic device of 3 cm wide and 9 cm long having a substantially rectangular addition port of 3 to 5 mm×8 to 15 mm (24 to 75 mm$^2$) is an immunochromatographic device having a wide addition port and is capable of exerting the effects of the immunochromatographic device of the present invention. The longer sides of the addition port are sides parallel to the longer sides of the chromatographic test piece, namely, sides along the flow direction of a specimen sample solution. The length of the longer side of the addition port is also referred to as an addition port length, and the length of the shorter side thereof is also referred to as an addition port width. In the above-described example, a substantially rectangular addition port is used. However, the shape of the addition port may be a triangular or round shape. When the size of the addition port of the immunochromatographic device of the present invention is indicated by area, the area is 24 to 75 mm$^2$, preferably 35 to 75 mm$^2$.

When a specimen is treated with a specimen treatment reagent established on an immunochromatographic test piece according to a conventional immunochromatography method, specimen-treating ability is weak due to a small area in which a sample solution is contacted with a region impregnated with the specimen treatment reagent. Furthermore, the specimen treatment is performed while the immunochromatographic test piece is gradually developed. Hence, a sample solution developed first and a sample solution developed later differ in the concentration of the specimen treatment reagent. Accordingly, the specimen treatment cannot be performed reliably.

The addition port of the immunochromatographic device of the present invention is established as a wide addition port and can therefore supply a large amount of specimen sample solution in a short time at once to a region impregnated with a specimen treatment reagent, namely, a region impregnated with a solid acid reagent or a region impregnated with a nitrous acid, upon immunochromatography. As a result, the extraction of the sugar chain antigen on the immunochromatographic test piece can be promoted. The amount of the specimen sample solution that can be supplied at once is 10 μL to 200 μL.

As a result, the difference in the concentration of the specimen treatment reagent caused by temporal difference does not occur. Hence, the specimen treatment upon immunochromatography can be promoted and performed reliably and efficiently.

The immunochromatographic device of the present invention is configured to have no space between the addition port and the sample pad positioned therebeneath so as to prevent a sample from escaping from the addition port.

The addition port of the immunochromatographic device of the present invention is established as a wide addition port and supplies a large amount of specimen sample solution in a short time at once. The edge portion, which is an outline, of an addition port has a given height (1 to 5 mm), and a supplied specimen sample solution is temporarily kept within the addition port.

As a result, it takes long for the specimen sample solution to be entirely absorbed to an immunochromatographic test piece, so that the sample solution may be escaped to the outside of the immunochromatographic test piece without being absorbed to the immunochromatographic test piece.

In the immunochromatographic device of the present invention, the sample pad is supported by a backing sheet having an outline size equivalent to or larger than that of the addition port, as a backing sheet supporting the sample pad, so as to prevent a sample from escaping from the addition port. Thus, the backing sheet can work to press the sample pad against the addition port to clear the space between the addition port and the sample pad. The immunochromatographic device thus configured can prevent a sample solution from escaping.

If the sample pad has an uneven thickness, a thin portion of the sample pad easily forms a space from the addition port and easily causes a sample solution to escape.

In the present invention, a pedestal for the container of the device can be designed as a high pedestal for the thin portion of the sample pad and designed as a low pedestal for the thick portion to eliminate the space between the addition port and the pad even having an uneven thickness. The immunochromatographic device thus configured can prevent a sample solution from escaping.

As a result, the extraction of the sugar chain antigen on the immunochromatographic test piece can be carried out efficiently.

Specifically, the present invention is as follows.

[1] An immunochromatographic device comprising an immunochromatographic test piece for extracting and measuring a sugar chain antigen in a specimen, and a container which stores the test piece, the immunochromatographic device having a specimen addition port in a sample pad of the test piece, the immunochromatographic test piece comprising: a sample pad to which a specimen mixed with nitrite or an acid solution is added; a label region comprising a labeled antibody obtained by labeling an antibody against the sugar chain antigen; and a detection region on which the antibody against the sugar chain antigen is immobilized, wherein an antibody-sugar chain antigen-labeled antibody complex is formed in the detection region to measure the sugar chain antigen, and the immunochromatographic test piece having a region impregnated with a neutralizing reagent upstream of the label region, and further having a region impregnated with a solid acid reagent when the specimen mixed with the nitrite is used, or a region impregnated with nitrite when the specimen mixed with the acid solution is used, upstream of the region impregnated with the neutralizing reagent, wherein the immunochromatographic device
  (i) has a wide specimen addition port for promoting the extraction of the sugar chain antigen with the nitrite and the solid acid reagent by retaining an added specimen sample solution and supplying the specimen sample solution in a short time to the region impregnated with the solid acid reagent or the nitrite, and
  (ii) has no space between the addition port and the sample pad so as to prevent the sample from escaping from the addition port.

[2] The immunochromatographic device according to the above [1], wherein the specimen addition port of the immunochromatographic device has a size of 24 to 75 mm$^2$.

[3] The immunochromatographic device according to the above [1] or [2], wherein the pad impregnated with the solid acid reagent or the nitrite, or the neutralizing reagent on the immunochromatographic test piece is made of a highly hydrophobic material, and the extraction of the sugar chain antigen with the nitrite and the solid acid reagent is promoted by slowing a development time of the specimen sample solution.

[4] The immunochromatographic device according to the above [3], wherein the highly hydrophobic material is selected from the group consisting of polyethylene, polyester, polystyrene, polypropylene, rayon, and nylon.

[5] The immunochromatographic device according to the above [1] or [2], wherein the pad impregnated with the solid acid reagent or the nitrite, or the neutralizing reagent on the immunochromatographic test piece is made of a material having a high degree of hydrophilicity, and the extraction of the sugar chain antigen with the nitrite and the solid acid reagent is promoted by slowing a development time of the specimen sample solution.

[6] The immunochromatographic device according to the above [5], wherein the material having a high degree of hydrophilicity is a thick filter.

[7] The immunochromatographic device according to any one of the above [1] to [6], wherein the extraction of the sugar chain antigen with the nitrite and the solid acid reagent is promoted by adding a surfactant to the pad impregnated with the solid acid reagent or the nitrite, or the neutralizing reagent on the immunochromatographic test piece, and adjusting the development time of the specimen sample solution.

[8] The immunochromatographic device according to the above [7], wherein the surfactant is selected from the group consisting of polyoxyethylene octyl phenyl ether, polyoxyethylene sorbitan fatty acid ester, polyoxyethylene alkyl ether, sodium cholate, deoxycholic acid, sodium lauryl sulfate, and sodium dodecylbenzenesulfonate.

[9] The immunochromatographic device according to any one of the above [1] to [8], wherein the extraction of the sugar chain antigen with the nitrite and the solid acid reagent is promoted by adding a high-molecular-weight compound having immobilizing action to the pad impregnated with the solid acid reagent or the nitrite, or the neutralizing reagent on the immunochromatographic test piece, and adjusting the development time of the specimen sample solution.

[10] The immunochromatographic device according to the above [9], wherein the high-molecular-weight compound having immobilizing action is PVA or PLL.

[11] The immunochromatographic device according to any one of the above [1] to [10], wherein the region impregnated with the solid acid reagent or the nitrite is present on the sample pad or on the pad with the label region applied thereto.

[12] The immunochromatographic device according to any one of the above [1] to [11], wherein the solid acid reagent is selected from the group consisting of malonic acid, malic acid, maleic acid, citric acid, and tartaric acid.

[13] The immunochromatographic device according to any one of the above [1] to [12], wherein the neutralizing reagent is tris(hydroxymethyl)aminomethane or sodium hydroxide.

[14] The immunochromatographic device according to any one of the above [1] to [13], wherein the sugar chain antigen is the sugar chain antigen of protozoa, fungi, bacteria, *Mycoplasma, Rickettsia, Chlamydia*, or virus.

[15] A method of measuring a sugar chain antigen in a specimen according to an immunochromatography method using the immunochromatographic device according to any one of the above [1] to [14],
  the method measuring the sugar chain antigen in the specimen by promoting the extraction of the sugar chain antigen according to the immunochromatography method, and the method comprising
mixing the specimen with a nitrous acid solution when the immunochromatographic device has a region impregnated with a solid acid reagent, or mixing the specimen with an acid solution when the immunochromatographic device has a region impregnated with nitrite, and adding the mixture to a sample pad of the immunochromatographic device, wherein in the immunochromatography method,
  the sugar chain antigen is extracted from the specimen by the action of nitrous acid generated through a reaction of the nitrite with the solid acid reagent in the region impregnated with the solid acid reagent or the region impregnated with the nitrite, the acid solution containing the sugar chain antigen is neutralized in a region impregnated with a neutralizing reagent, and an antibody-sugar chain antigen-labeled antibody complex is formed in a detection region.

EXAMPLES

The present invention will be specifically described in the following examples. However, these examples are not intended to limit the scope of the present invention.

In the following examples, % represents w/v % unless otherwise specified.

Example 1

1. Immobilization of Anti-*Streptococcus pyogenes* (Group a β-Hemolytic *Streptococcus*) Antibody on Nitrocellulose Membrane (Support)

A solution obtained by diluting an anti-*Streptococcus pyogenes* antibody with purified water to a concentration of 1.0 mg/mL and an anti-rabbit IgG antibody were prepared. The anti-*Streptococcus pyogenes* antibody was linearly applied to the sample pad side of a nitrocellulose membrane backed with a PET (polyethylene terephthalate) film, and the anti-rabbit IgG antibody was linearly applied to the absorption band side thereof. Thereafter, the nitrocellulose membrane was dried at 45° C. for 30 minutes to obtain an anti-*Streptococcus pyogenes* antibody-immobilized membrane. This membrane is referred to as an "antibody-immobilized membrane" in the present example.

2. Immobilization of Anti-*Streptococcus pyogenes* Antibody on Colored Polystyrene Particles An anti-*Streptococcus pyogenes* antibody was diluted with purified water to a concentration of 1.0 mg/mL, and colored polystyrene particles were then added to the obtained solution to a concentration of 0.1%, followed by stirring. Thereafter, carbodiimide was added to the mixed solution to a concentration of 1%, and the obtained mixture was further stirred. A supernatant was removed from the reaction mixture by a centrifugal operation, and was then re-suspended in 50 mM Tris (pH 9.0) and 3% BSA to obtain a 0.04% anti-*Streptococcus pyogenes* antibody-bound colored polystyrene particle suspension. These particles are referred to as "antibody-immobilized particles" in the present example.

3. Application and Drying of Anti-*Streptococcus pyogenes* Antibody-Bound Colored Polystyrene Particles The antibody-immobilized particle suspension produced in the above 2 was applied in a predetermined amount to a non-woven fabric, and was then dried at 45° C. for 30 minutes. The obtained non-woven fabric is referred to as a "dry pad" in the present example.

4. Application of Neutralizing Reagent (Basic Reagent) Pad

3 M Trizma (brand name) Base (Tris base) as a neutralizing reagent (basic reagent), and 1.5% Triton X-100 were applied in a concentration of 30 μL/cm to a filter (Toyo Roshi Kaisha, Ltd.; No. 26-3).

5. Production of Solid Acid Reagent Pad 1.0 M tartaric acid as a solid acid reagent, and 0.5% Triton X-100 were applied in a concentration of 13 μL/cm to a non-woven fabric (Unitika, Ltd.; Elves). Immediately after the application, the non-woven fabric was dried at 45° C. for 1 hour to obtain a solid acid reagent-impregnated non-woven fabric.

6. Production of Immunochromatographic Test Piece for *Streptococcus pyogenes* Detection The antibody-immobilized membrane produced in the above 1, the dry pad produced in the above 3, and the neutralizing reagent (basic reagent) pad produced in the above 4 were each adhered to other members (a backing sheet and an absorption band), followed by cutting the resultant into a piece with a width of 5 mm, thereby producing a test piece for detecting *Streptococcus pyogenes*. In the present example, a test piece, in which the solid acid reagent- and neutralizing reagent (basic reagent)-impregnated filters are used as a sample pad, are referred to as "the present immunochromatographic test piece." It is to be noted that the immunochromatographic test piece comprises, from a site upstream thereof, a solid acid reagent-impregnated non-woven fabric, a neutralizing reagent (basic reagent)-impregnated non-woven fabric, a dry pad (label region), an antibody-immobilized membrane (detection region), and an absorption band, along the flow of a specimen.

7. Measurement

As a negative specimen, 75 μL of a 2 M sodium nitrite solution supplemented with a pH indicator (phenol red) was added dropwise to the present immunochromatographic test piece, and 5 minutes to 60 minutes later, judgment was made.

The results are shown in Table 1.

From the results shown in Table 1, it was revealed that a member having the following properties is preferred as a member to which a neutralizing reagent (basic reagent) is applied.

(1) Physical Characteristics (Basis Weight and Thickness)

10 to 400 g/m$^2$ and a thickness of 0.1 to 2.0 mm, preferably a basis weight of 50 to 300 g/m$^2$ and a thickness of 0.4 to 0.8 mm, more preferably a basis weight of approximately 250 g and a thickness of approximately 0.6 mm.

(2) Water-Absorbable Property

Having a water-absorbable property with an amount of water absorbed (per cm$^2$) of 10 μl/cm$^2$ to 100 μl/cm$^2$ and a water absorption speed of 1.0 μl/sec to 5 μl/sec, preferably an amount of water absorbed of 30 μl/cm$^2$ or more and a water absorption speed of 2 μl/sec or less, more preferably an amount of water absorbed of 30 μl/cm$^2$ or more and a water absorption speed of 1.5 μl/sec or less.

(3) Water-Retainable Property

Having a water-absorbable property with a water-retainable property (per cm$^2$) of 3 μl/cm$^2$ to 100 μl/cm$^2$, preferably 15 μl/cm$^2$ or more, after 5-minute contact with a membrane in a wet state.

The physical characteristics and the water-absorbable property need to fall within the above-described ranges, and the water-retainable property or retentivity is not an essential property. However, it is preferable to have both the water-retainable property and the retentivity.

TABLE 1

| Product name | Manufacturer | Item number | Material | Physical characteristics | | | | Characteristics Water-absorbable property | | | |
|---|---|---|---|---|---|---|---|---|---|---|---|
| | | | | Basis weight (g/m²) | Thickness (mm) | Dry Tensile Strength (dryN/50 mm) | | Time to reach distal end (sec)*2-1 | Amount of water absorbed (μl)*2-2 | Water absorption speed (mobility) (μl/sec)*2-3 | Amount of water absorbed (μl/cm²) |
| | | | | | | M.D | C.D. | | | | |
| Bemlise | Asahi Kasei Corp. | SE103 | Cupra (cupro) | 100 | 0.54 | 66 | 29.3 | 40 | 188 | 4.7 | 62.7 |
| | | TA30B | | 38 | 0.35 | 26.1 | 21 | 60 | 75 | 1.3 | 25.0 |
| | | SR60 | *1 | 60 | 0.47 | 34.4 | 28.2 | 60 | 125 | 2.1 | 41.7 |
| Eltas Nyron | | N01130 | Nylon | | 0.61 | 550 | 210 | 120 | 150 | 1.3 | 50.0 |
| Elves | Unitika, Ltd. | S1003/WDO | PET | 100 | 0.50 | 400 | 170 | N.D. | N.D. | N.D. | N.D. |
| Wet length filter | Toyo Roshi Kaisha, Ltd. | No. 26-3 | Paper | 260 | 0.58 | | | 185 | 197 | 1.1 | 65.7 |
| Filter for viscous solution | | No. 462 | Paper | 168 | 0.53 | | | 125 | 165 | 1.3 | 55.0 |

| Product name | Manufacturer | Item number | Material | Characteristics Water-retainable property | | Detection region neutrality duration time | Summary | | | |
|---|---|---|---|---|---|---|---|---|---|---|
| | | | | Amount of water retained (μl/1 cm²)*3 | Retentivity Liquid spread area (mm²)*4 | | Water absorption speed (mobility) | Amount of water absorbed | Water-retainable property | Retentivity |
| Bemlise | Asahi Kasei Corp. | SE103 | Cupra (cupro) | 10 | 25 | 15 min | Rapid | ○ | Δ | Δ |
| | | TA30B | | 5 | 30 | 10 min | Slow | X | X | X |
| | | SR60 | *1 | 2 | 27 | 15 min | Normal | Δ | X | Δ |
| Eltas Nyron | | N01130 | Nylon | 3 | 30 | 17 min | Slow | ○ | X | X |
| Elves | Unitika, Ltd. | S1003/WDO | PET | 0 | 30 | 5 min | ? | ? | X | X |
| Wet length filter | Toyo Roshi Kaisha, Ltd. | No. 26-3 | Paper | 18 | 15 | 40 min | Slow | ○ | ○ | ○ |
| Filter for viscous solution | | No. 462 | Paper | 3 | 20 | 20 min | Slow | ○ | X | ○ |

REFERENCE SIGNS LIST

1 Support (comprising a detection region)
2 Label region
3 Detection region
4 Sample pad
5 Solid acid reagent region
6 Neutralizing reagent region
7 Absorption band
8 Backing sheet Using the immunochromatographic device of the present invention, group A β-hemolytic *Streptococcus* can be detected with high sensitivity.

All publications, patents, and patent applications cited in the present description are incorporated herein by reference in their entirety.

The invention claimed is:

1. An immunochromatographic test piece for extracting and measuring a sugar chain antigen of microorganisms belonging to genus *Streptococcus* in a specimen, the immunochromatographic test piece comprising: a sample pad to which a specimen mixed with nitrite or an acid solution is added; a label region comprising a labeled antibody obtained by labeling an antibody against the sugar chain antigen; and a detection region on which the antibody against the sugar chain antigen is immobilized, wherein an antibody-sugar chain antigen-labeled antibody complex is formed in the detection region to measure the sugar chain antigen, and the immunochromatographic test piece having a region impregnated with a neutralizing reagent upstream of the label region, and further having a region impregnated with a solid acid reagent when the specimen mixed with the nitrite is used, or a region impregnated with nitrite when the specimen mixed with the acid solution is used, upstream of the region impregnated with the neutralizing reagent, wherein
  a material for the region impregnated with the neutralizing reagent is a filter or a glass filter having three properties of being highly absorbable, being highly water-retainable, and being low releasable or continuously releasable, wherein the material for the region impregnated with the neutralizing agent has a basis weight of 50 to 300 g/m² and a thickness of 0.21 to 0.8 mm, and which absorbs water in an amount of 30 to 100 μl/cm² per cm/m², has a water absorption speed of 1.0 to 2.0 μl/sec, retains water in an amount of 15 to 100 $\mu l/cm^2$ after a fragment of 1 $cm/m^2$ is allowed to come in a wet state into contact with the detection region and left standing for 5 minutes, and has a liquid spread area of 20 $mm^2$ or smaller after a fragment of 1 $cm/m^2$ is allowed to come in a wet state into contact with a membrane and left standing for 5 minutes, and owing to the high water-absorbable property and the high water-retainable property of the region impregnated with the neutralizing reagent, the acid solution containing the sugar chain antigen is neutralized, and owing to the low releasable property or the sustained releasable property of the region impregnated with the neutralizing reagent, a remaining acid solution is prevented from arriving at the detection region, or a neutralized test solution is continuously developed to the detection region, so that a non-specific reaction is suppressed.

2. The immunochromatographic test piece according to claim 1, wherein the material for the region impregnated with the neutralizing reagent has a basis weight of 250 to 270 $g/m^2$.

3. The immunochromatographic test piece according to claim 1, wherein owing to the high water-absorbable property and the high water-retainable property of the region impregnated with the neutralizing reagent, the acid solution containing the sugar chain antigen is neutralized, and owing to the sustained releasable property of the region impregnated with the neutralizing reagent, a sufficient neutralizing ability is maintained even when a remaining acid solution arrives at the detection region, so that a non-specific reaction is suppressed.

4. The immunochromatographic test piece according to claim 1, wherein owing to the high water-absorbable property and the high water-retainable property of the region impregnated with the neutralizing reagent, the acid solution containing the sugar chain antigen is neutralized, and owing to the low releasable property of the region impregnated with the neutralizing reagent, a remaining acid solution is prevented from arriving at the detection region, so that a non-specific reaction is suppressed in a negative case, and color development of a line is prevented at or after the time of judgment in a positive case.

5. The immunochromatographic test piece according to claim 1, wherein the region impregnated with the solid acid reagent or the nitrite is present on the sample pad or on the pad with the label region applied thereto.

6. The immunochromatographic test piece according to claim 1, wherein the solid acid reagent is selected from the group consisting of malonic acid, malic acid, maleic acid, citric acid, and tartaric acid.

7. The immunochromatographic test piece according to claim 1, wherein the neutralizing reagent is tris(hydroxymethyl)aminomethane or sodium hydroxide.

8. The immunochromatographic test piece according to claim 1, wherein the material for the region impregnated with the neutralizing reagent has a thickness of 0.4 mm to 0.8 mm.

* * * * *